(12) United States Patent
Ben-Haim

(10) Patent No.: US 10,362,960 B2
(45) Date of Patent: Jul. 30, 2019

(54) MULTI POINT TREATMENT PROBES AND METHODS OF USING THEREOF

(71) Applicant: Renal Dynamics Ltd., Road Town (VG)

(72) Inventor: Shlomo Ben-Haim, London (GB)

(73) Assignee: Renal Dynamics Ltd., Road Town, Virgin Islands (GB)

(*) Notice: Subject to any disclaimer, the term of this patent is extended or adjusted under 35 U.S.C. 154(b) by 1081 days.

(21) Appl. No.: 14/652,117

(22) PCT Filed: Dec. 19, 2013

(86) PCT No.: PCT/IL2013/051045
§ 371 (c)(1),
(2) Date: Jun. 14, 2015

(87) PCT Pub. No.: WO2014/097300
PCT Pub. Date: Jun. 26, 2014

(65) Prior Publication Data
US 2015/0320492 A1 Nov. 12, 2015

Related U.S. Application Data

(60) Provisional application No. 61/739,744, filed on Dec. 20, 2012.

(51) Int. Cl.
*A61B 5/00* (2006.01)
*A61B 5/053* (2006.01)
(Continued)

(52) U.S. Cl.
CPC .............. *A61B 5/0538* (2013.01); *A61B 5/05* (2013.01); *A61B 5/4872* (2013.01);
(Continued)

(58) Field of Classification Search
CPC ................................ A61B 5/0538; A61B 5/05
(Continued)

(56) References Cited

U.S. PATENT DOCUMENTS 4,271,848 A 6/1981 Turner et al.
4,448,198 A 5/1984 Turner
(Continued)

FOREIGN PATENT DOCUMENTS

EP 0519250 12/1992
EP 2452648 5/2012
(Continued)

OTHER PUBLICATIONS

Communication Relating to the Results of the Partial International Search dated Dec. 10, 2014 From the International Searching Authority Re. Application No. PCT/IB2014/063924.
(Continued)

*Primary Examiner* — Nadia A Mahmood

(57) ABSTRACT

An embodiment of system for intrabody treatment of a treatment location in a body of a treated patient is disclosed. The system may include deploying at least two transmission points of a multi point probe to a proximity with the treatment location in the body. A transmission pattern may be selected that defines, for each of the transmission points, a respective signal of a plurality of transmission signals. The transmission pattern may form at least one interaction between the respective signals. The interaction may form a hot spot at the treatment location. A plurality of transmission signals may be delivered from the transmission points.

28 Claims, 7 Drawing Sheets

(51) Int. Cl.
  *A61B 18/12* (2006.01)
  *A61B 5/05* (2006.01)
  *A61B 18/14* (2006.01)
  *A61B 18/00* (2006.01)
  *A61B 18/18* (2006.01)

(52) U.S. Cl.
  CPC .......... *A61B 5/6852* (2013.01); *A61B 5/7278* (2013.01); *A61B 18/1206* (2013.01); *A61B 18/1492* (2013.01); *A61B 5/6853* (2013.01); *A61B 5/6856* (2013.01); *A61B 5/6859* (2013.01); *A61B 2018/0016* (2013.01); *A61B 2018/0022* (2013.01); *A61B 2018/0075* (2013.01); *A61B 2018/00214* (2013.01); *A61B 2018/00267* (2013.01); *A61B 2018/00577* (2013.01); *A61B 2018/00642* (2013.01); *A61B 2018/00702* (2013.01); *A61B 2018/00732* (2013.01); *A61B 2018/00779* (2013.01); *A61B 2018/00839* (2013.01); *A61B 2018/00875* (2013.01); *A61B 2018/00904* (2013.01); *A61B 2018/124* (2013.01); *A61B 2018/1435* (2013.01); *A61B 2018/1467* (2013.01); *A61B 2018/1861* (2013.01); *A61B 2018/1884* (2013.01)

(58) Field of Classification Search
  USPC .......................................................... 607/67
  See application file for complete search history.

(56) References Cited

U.S. PATENT DOCUMENTS

| | | | |
|---|---|---|---|
| 4,589,423 | A | 5/1986 | Turner |
| 4,679,980 | A | 7/1987 | Bland |
| 4,798,215 | A | 1/1989 | Turner |
| 5,100,423 | A | 3/1992 | Fearnot |
| 5,284,144 | A | 2/1994 | Delannoy et al. |
| 6,673,090 | B2 | 1/2004 | Root et al. |
| 7,326,226 | B2 | 2/2008 | Root et al. |
| 7,749,220 | B2 | 7/2010 | Schmaltz |
| 7,766,960 | B2 | 8/2010 | Alexander et al. |
| 8,444,665 | B2 | 5/2013 | Tsugita |
| 2005/0096647 | A1* | 5/2005 | Steinke .............. A61B 18/1492 606/41 |
| 2006/0241704 | A1 | 10/2006 | Shuros et al. |
| 2007/0118193 | A1 | 5/2007 | Turner et al. |
| 2008/0118193 | A1 | 5/2008 | Chen et al. |
| 2011/0196410 | A1 | 8/2011 | Besselink et al. |
| 2011/0238083 | A1 | 9/2011 | Moll et al. |
| 2012/0172680 | A1 | 7/2012 | Gelfand et al. |
| 2012/0184952 | A1 | 7/2012 | Jenson et al. |
| 2012/0203265 | A1 | 8/2012 | Heuser |
| 2013/0030430 | A1 | 1/2013 | Stewart et al. |
| 2013/0066316 | A1 | 3/2013 | Steinke et al. |
| 2014/0018788 | A1 | 1/2014 | Engelman et al. |

FOREIGN PATENT DOCUMENTS

| | | |
|---|---|---|
| EP | 2495012 | 9/2012 |
| JP | H04221544 | 8/1992 |
| WO | WO 03/053259 | 7/2003 |
| WO | WO 2008/039684 | 4/2008 |
| WO | WO 2008/113857 | 9/2008 |
| WO | WO 2010/118064 | 10/2010 |
| WO | WO 2011/055143 | 5/2011 |
| WO | WO 2011/144760 | 11/2011 |
| WO | WO 2013/028781 | 2/2013 |
| WO | WO 2013/134479 | 9/2013 |
| WO | WO 2014/005155 | 1/2014 |
| WO | WO 2014/097300 | 6/2014 |
| WO | WO 2014/118733 | 8/2014 |
| WO | WO 2014/118785 | 8/2014 |
| WO | WO 2015/022668 | 2/2015 |

OTHER PUBLICATIONS

Communication Relating to the Results of the Partial International Search dated Feb. 18, 2015 From the International Searching Authority Re. Application No. PCT/IB2014/063924.
International Preliminary Report on Patentability dated Jul. 2, 2015 From the International Bureau of WIPO Re. Application No. PCT/IL2013/051045.
International Search Report and the Written Opinion dated Apr. 16, 2014 From the International Searching Authority Re. Application No. PCT/IL2013/051045.
International Search Report and the Written Opinion dated Apr. 28, 2015 From the International Searching Authority Re. Application No. PCT/IB2014/063924.
Bakhiet et al. "A Novel Nervous System-Induced Factor Inducing Immune Responses in the Spleen", Immunology and Cell Biology, 86: 688-699, 2008.
Bakhiet et al. "Modulation of Immune Responses and Suppression of Experimental Autoimmune Myasthenia Gravis by Surgical Denervation of the Spleen", Clinical and Experimental Immunology, 144(2): 290-298, 2006.
Blair et al. "Carotid Body Denervation, Too Soon to Get Breathless About Heart Failure?", Journal of the American College of Cardioloy, 62(25): 2431-2432, 2013.
Boyle et al. "Role of the Central Nervous System (CNS) in Peripheral Inflammation: Sympathetic Innervation of the Spleen Regulates Inflammatory Arthritis", Arthritis & Rheumatism, 62: Abstract Supplement, Abstracts of the American College of Rheumatology/Association of Rheumatology Health Professionals Annual Scientific Meeting, Atlanta, GA, USA, Nov. 6-11, 2010, 1 P., Nov. 2010.
Bujis et al. "Spleen Vagal Denervation Inhibits the Production of Antibodies to Circulating Antigens", PLoS ONE, 3(9): e3152-1-e3152-8, Sep. 2008.
Daglilar et al. "Controlled Swine Bile Duct Ablation With a Bipolar Radiofrequency Catheter", Gastrointestinal Endoscopy, 77(5): 815-819, 2013.
Mauri et al. "Devices for Distal Protection During Percutaneous Coronary Revascularization", Circulation, 113: 2651-2656, 2006.
Rasouli et al. "Brain-Spleen Inflammatory Coupling: A Literature Review", The Einstein Journal of Biology and Medicine, EJBM, 27(2): 74-77, 2011.
Rosas-Ballina et al. "Acetylcholine-Synthesizing T Cells Relay Neural Signals in a Vagus Nerve Circuit", Science,334(6052): 98-101, Published Online Sep. 15, 2011.
Rosas-Ballina et al. "Splenic Nerve Is Required for Cholinergic Antiinflammatory Pathway Control of TNF in Endotoxemia", Proc. Natl. Acad. Sci. USA, PNAS, 105(31): 11008-11013, Aug. 5, 2008.
Siewiorek et al. "The Angioguard™ Embolic Protection Device", Expert Review of Medical Devices, 5(3): 287-296, May 2008.
Waldburger et al. "Regulation of Peripheral Inflammation by the Central Nervous System", Current Rheumatology Reports, 12(5): 370-378, Oct. 2010.
International Preliminary Report on Patentability dated Feb. 25, 2016 From the International Bureau of WIPO Re. Application No. PCT/IB2014/063924.

\* cited by examiner

MULTI POINT TREATMENT PROBES AND METHODS OF USING THEREOF

FIELD AND BACKGROUND OF THE INVENTION

The present invention, in some embodiments thereof, relates to multi point probes for medical treatment and, more particularly, but not exclusively, to multi point probes for a tissue treatment, such as ablation.

During the last years, various radio frequency ('RF') based tissues treatments, such as RF ablation, have been developed. In these treatments a part of an organ and/or a tissue, for example a cancerous tissue or a dysfunctional and/or over functional tissue, is ablated using a heat generated from high frequency alternating current that does not directly stimulate nerves or heart muscle and can be used without general anesthetic. These treatments are usually performed under image guidance, such as X-ray screening, computerized tomography (CT) scan and ultrasound, by physician, such as an interventional pain specialist (such as an anesthesiologist), interventional radiologist, a gastrointestinal a surgical endoscopist, and a cardiac electrophysiologist.

SUMMARY OF THE INVENTION

According to an aspect of some embodiments of the present invention there is provided a method of intrabody treating a treatment location in a body of a treated patient, including deploying at least two transmission points of a multi point probe to a proximity with the treatment location in the body; selecting a transmission pattern that defines, for each of the at least two transmission points, a respective signal of a plurality of radio frequency transmission signals, the transmission pattern forms at least one interaction between the respective signals; wherein the at least one interaction is selected to form at least one hot spot at the treatment location; and delivering the respective signals from the at least two transmission points.

According to some embodiments of the invention, the delivering of the respective signals is concurrent.

According to some embodiments of the invention, the selecting further includes selecting a timing for the delivering and the delivering of at least two of the respective signals is at different times. The different times may be chosen to increase interaction for a target selected from the group consisting of a particular chemical, a particular tissue and a particular location.

According to some embodiments of the invention, the delivering of each of at least two of the interacting respective signals is from a different respective points of the at least two transmission points.

According to some embodiments of the invention, the at least one interaction is selected from the group consisting of constructive interference, spatial interaction, temporal interaction, signal correlation, resonance and destructive interference that defines the at least one hot spot.

According to some embodiments of the invention, the selecting a transmission pattern comprises defining at least one of a phase, frequency and input power of each the respective signal.

According to some embodiments of the invention, the multi point probe includes a plurality of receiving points for intercepting energy delivered from the at least two transmission points via the treatment location and the method may further include measuring the intercepted energy.

According to some embodiments of the invention, the method may further include creating a map of a dielectric property in at least a part of the treatment location according to an analysis of the intercepted energy.

According to some embodiments of the invention, the transmission pattern is selected according to a result of the measuring.

According to some embodiments of the invention, the method may further include measuring a complex impedance that includes real and imaginary parts at least one of the transmission points and the selecting may be performed according to both the real and imaginary parts.

According to some embodiments of the invention, the selecting is performed according to a combination of the map and an anatomical map mapping of at least part of the treatment location.

According to some embodiments of the invention, the delivering comprises detecting changes in a dielectric property of the treatment location or of data received by a receiving point and an adjustment of the delivering according to the detecting.

According to some embodiments of the invention, the delivering comprises transmitting three different the respective signals from three different transmission points.

According to some embodiments of the invention, the delivering is simultaneous.

According to some embodiments of the invention, at least one of the at least two transmission signals includes a microwave band signal.

According to some embodiments of the invention, the method may further include directing the delivering with an artificial dielectric located inside the patient.

According to an aspect of some embodiments of the present invention there is provided a system of intrabody treatment, including: a multi point probe transported by a catheter to a lumen of a body of a treated patient, the multi point probe having at least two transmission points; and a processor configured to select a transmission pattern including for each of the at least two transmission points, a respective signal of a plurality of radio frequency transmission signals, the transmission pattern forms at least one interaction between the respective signals from the at least two transmission points, the at least one interaction defines at least one hot spot at the treatment location; and controlling delivery of the respective signals from the transmission points.

According to some embodiments of the invention, the processor determines a timing for each of the respective signals.

According to some embodiments of the invention, the processor selects the respective signals to interact concurrently.

According to some embodiments of the invention, the multi point probe has a supporting structure having a compressed state to allow placing the multi point probe in a lumen of the catheter and a deployed stated that place the at least two transmission points away from one another and from a longitudinal axis of the lumen.

According to some embodiments of the invention, the multi point probe includes one or more receiving points supported by the supporting structure intercepting an energy from the treatment location.

According to some embodiments of the invention, at least one of the one or more receiving points is also one of the at least two transmission points.

According to some embodiments of the invention, the system may further include an energy source controlled by the processor; the energy source supplying the respective signals to the transmission points.

According to an aspect of some embodiments of the present invention there is provided a method of intrabody imaging in a body of a treated patient, including: inserting a probe into the body, the probe including at least two transmission points; delivering a radio frequency transmission signal from the at least two transmission points into the treatment location; intercepting by at least one receiving point a feedback from at least one of the respective signals via the treatment location; and reconstructing at least one dielectric property of the tissue and of at least one additional tissue in the treatment location based on the intercepted feedback.

According to some embodiments of the invention, the reconstructing comprises identifying fat areas.

According to some embodiments of the invention, the reconstructing comprises identifying a movement of the probe.

According to some embodiments of the invention, the delivering comprises transmitting in sequence from at least three different transmission points of the probe.

According to some embodiments of the invention, method may further include directing the delivering with an artificial dielectrics located inside the patient.

According to some embodiments of the invention, each the transmission point is separately connected to an EM energy source for separately receiving one of the plurality of transmission signals.

According to some embodiments of the present invention there is provided a method of ablating an intrabody target tissue. The method comprises ablating determining a treatment location having an intrabody target tissue in a body of a treated patient, maneuvering a multi point probe having at least two transmission points to a proximity with the treatment location in the body, measuring impedance in each the transmission point, selecting a transmission pattern that defines, for each the transmission point and according to the impedance, one of a plurality of transmission feeds so as to form at least one hot spot on the intrabody target tissue, and simultaneously delivering the plurality of transmission feeds from the plurality of transmission points to ablate the intrabody target tissue.

According to some embodiments of the present invention there is provided a multi point probe for intrabody treatment. The multi point probe comprises an array of at least two transmission points, a support structure which is sized and shaped to support the at least two transmission points on a tip of a catheter, and a plurality of conducting wires which allows separately providing each the transmission point with one of a plurality of transmission feeds. The at least two transmission points forms a constructive and destructive interference that defines at least one hot spot at a treatment location by simultaneously delivering the plurality of transmission feeds.

Optionally, the supporting structure has a compressed state to allow placing the multi point probe in a lumen of the catheter and a deployed stated that sends the at least two transmission points away from one another and from a longitudinal axis of the lumen.

Optionally, the supporting structure is selected from a group consisting of a helical structure, a spiral structure, a branched structure.

Optionally, the supporting structure is made of a shape memory alloy.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system.

In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

Figure 1:
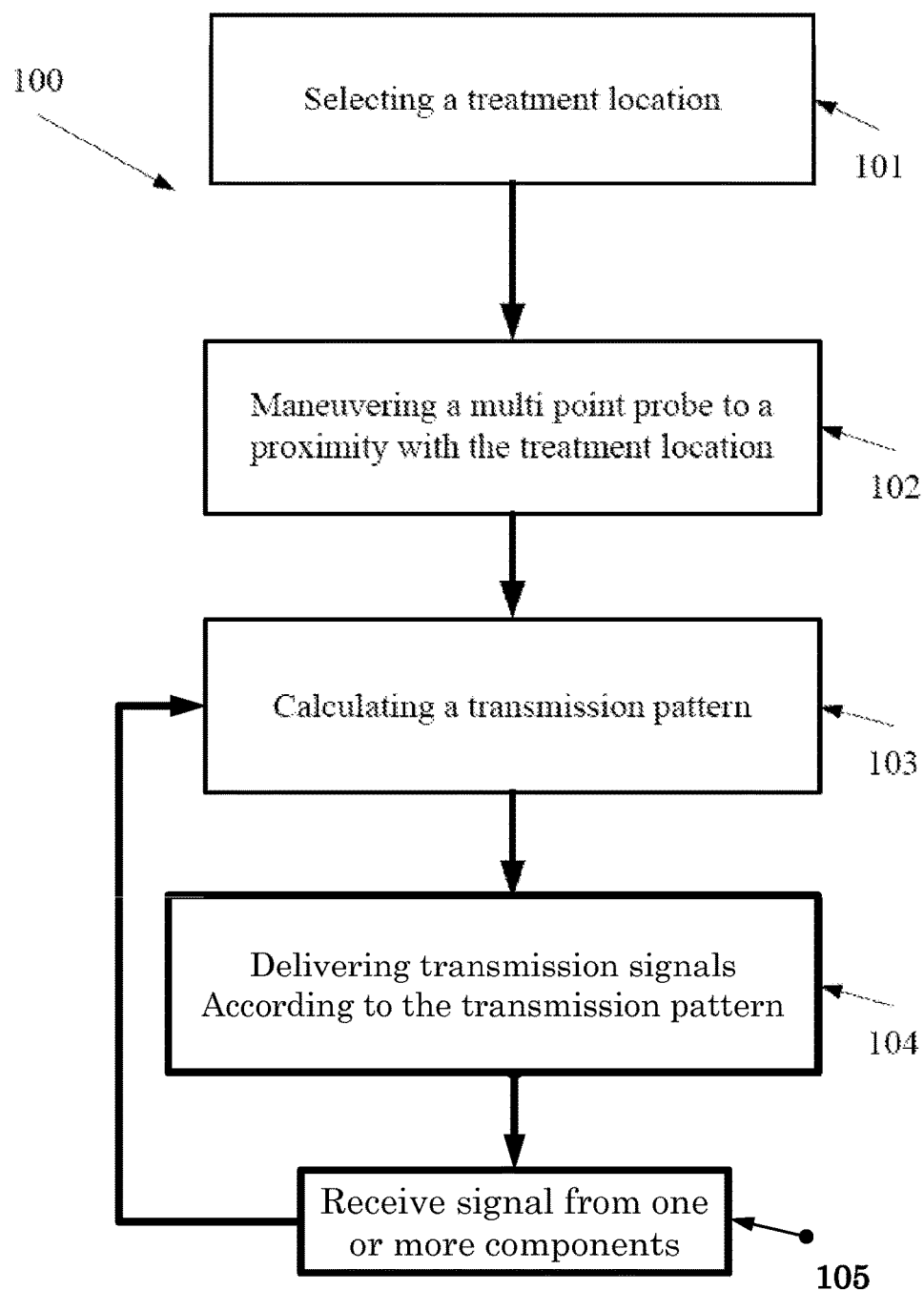
FIG. 1 is a flowchart of a method of treating an intrabody tissue, according to some embodiments of the present invention.

The present invention, in some embodiments thereof, relates to multi point probes for medical treatment and, more particularly, but not exclusively, to multi point probes for a tissue treatment, such as ablation.

According to some embodiments of the present invention, there are provided methods and devices of forming an electromagnetic (EM) field with interaction(s) between transmitted signals, for example constructive and/or destructive interference(s), that defines one or more hot spots at an intrabody treatment location using a multi point probe with two or more transmission points and optionally receiving points, for example 3 or more. In use, the multi point probe may be brought to proximity with the intrabody treatment location, for example to a distance of 2 centimeters or less, for instance using a catheter. In some embodiments, based on a transmission pattern that is calculated with respect to the intrabody treatment location, a plurality of respective transmission signals are delivered from each of the transmission points. For example each respective signal may be an RF signal in the radio and/or microwave band. Optionally the respective signals may be tuned to interact through constructive and/or destructive interference and/or resonance.

Optionally, the interaction may be dependent on tissue properties and/or location. Optionally two interacting signals may be correlated to interact to produce a greater effect on a target tissue than non-target tissue. As used herein the term transmission pattern may refer to and/or include and/or define a set of signals delivered from the transmission points. According to the pattern, each transmission point may transmit a respective signal of a plurality of transmission signals. The transmission pattern optionally defines the frequency, phase, modulation, timing and/or period of each respective signal for one or more transmission points. Transmission signals may optionally be transmitted simultaneously, concurrently and/or at different times (e.g. consecutively). Optionally, the transmission pattern may be calculated prior to a medical procedure, for example based on extrabody imaging data and/or known tissue properties.

Alternatively or additionally, the transmission pattern may be calculated and/or modified during a medical procedure, for example based on a test session and/or based on feedback from a treatment. For example, a test session may include delivering a plurality of test signals (signals optionally intended to reveal properties in and/or around a treatment location without necessarily having a therapeutic effect). The test signals may be iteratively emitted from the transmission points and intercepted by receiving points, for instance transmitted from one transmission point in an array of transmission and receiving points of the probe, for example antennas, and intercepted by the same antennas and/or other antennas of the array. Optionally, the transmission pattern is set according to dielectric properties of the tissues in the treatment location. In some embodiments, certain tissues, for example a nervous tissue may be targeted while respective surrounding tissues remain intact. Alternatively unhealthy tissue, for example cancerous tissue, may be targeted with healthy tissue remains intact.

Optionally, the transmission points of the multi point probe are distributed on a support structure. The support structure may be designed to bring the transmission points to contact or substantially in contact with a wall of an intrabody lumen, for example a blood vessel, in proximity to the treatment location. For example, the support structure may distribute transmission points in a helical arrangement, a spiral arrangement, a semi hemisphere arrangement, and/or a tree shape arrangement and/or mounted on an oblong surface area. The multi port probe may be introduced into an inner volume of a tissue, for example connected to a needle having a plurality of receiving points thereon into an organ, for example a liver.

According to some embodiments of the present invention, there are provided methods and systems wherein a map of dielectric properties of a treatment location is generated using a multi point probe with two or more transmission points and optionally receiving points. In some embodiments the map may cover the treatment location and/or the treatment area. For example, the map may cover a 3D zone of length ranging between 1 mm and 3 cm. The map may optionally have a resolution fine enough to show a feature of length between 1.0 mm to 3.0 mm or larger. In some embodiments a map may cover a three dimensional volume, for example a volume ranging between 1 $mm^3$ to 10000 $mm^3$ (for example the volume around and/or between 1 or more electrodes). A map may optionally cover a two dimensional area for example ranging between 1 $mm^2$ to 1000 $mm^2$ (for example a cross section of tissue between two electrodes) and/or a one dimensional line of length ranging between 1 mm to 3 cm (for example a line of tissue between two electrodes). In use, after the multi point probe is brought to proximity with the intrabody treatment location, for example as outlined above and/or described below, signals are transmitted and/or intercepted by an array of antennas. The map may be generated by a set of equations that is based on the relationship between the intercepted and transmitted energy in the signals. In some embodiments, energy transmission (e.g., for treatment) is determined in accordance with or based on the map of dielectric properties of a treatment location or a part thereof. In some embodiments, feedback energy from the treatment may be intercepted by one or more receiving points. The feedback energy may be used to update the map of dielectric properties, to monitor the progress of treatment and/or to select a new transmission pattern for further treatment. A map may also include temporal information. For example the map may include information on dielectric properties of tissue in 1, 2 or 3 dimensions and their changes over time. For example a map may cover a time period of a treatment session. For example a map may cover a time period of between 30 seconds and 5 minutes and/or between 5 minutes and 30 minutes and/or between 30 minutes and an hour and/or between 1 hour and 5 hours.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1, which is a flowchart of a method 100 of treating an intrabody tissue, for instance ablating the intrabody tissue, according to some embodiments of the present invention. Treating may include forming (or otherwise generating) an electromagnetic (EM) field with interaction(s) between respective transmitted signals, for example destructive and optionally constructive interference(s). The EM field may be formed by delivering 104 a number of transmission signals of energy, for example RF energy or microwave energy, from a plurality of transmission points of a multi point probe. As used herein, a multi point probe is a probe with two or more transmission points, such as antennas, which may be also receiving points, for example as described below. For example, transmission points may function as receiving points or otherwise configured to intercept RF energy transmissions, e.g., from the treating location. For example, a multi point probe may include 2, 3, 5, 10, 20, 50, 100 or any intermediate or larger number of transmission points. For example, the multi point probe may include 3 transmission points. As used herein the term RF transmission pattern may refer to and/or include signals in the radio band and/or micro-wave band. The transmission may optionally include a signal in the radio frequency band, for example between about 500 kilohertz (kHz) and about 500 Mega Hertz (MHz), for example 500 kHz to 30,000 kHz, 500 kHz to 1 MHz, 30 MHz to 500 MHz.

Alternatively or additionally a transmission may include a signal in the microwave frequency band, for example between about 500 Mega Hertz (MHz) and about 300 Giga Hertz (GHz), for example 500 MHz to 700 MHz, 700 MHz to 1 GHz, 1 GHz to 3 GHz, 3 GHz to 10 GHz and/or 10 GHz to 300 GHz. Optionally, each transmission point includes an antenna with a diameter of few millimeters, for example 0.1 cm, 0.2 cm, 0.5 cm 1 cm or any intermediate or larger diameter. Optionally, each transmission point may include a radiating element or otherwise may have a structure that enables energy transmission. It should be noted that the term transmission point may comprise a plurality of subpoints arranged in a two dimensional (2D) and/or three dimensional (3D) structures, for example as a spiral or helical conductor. Optionally, the transmission points (e.g., points 202 illustrated for example in FIG. 2) are mounted to direct EM energy, such as RF energy to the side of the catheter, for example substantially perpendicular to a longitudinal axis thereof. The transmission points may be of the same structure or of different structures, e.g., the antenna diameter and/or geometry may vary between transmission points, the material of the transmission points may be different. The transmission points may have the same function or have a different function. In some embodiments, one or more transmission points may be configured to transmit energy at a first bandwidth (e.g., at a first frequency) while one or more other transmission points may be configured to transmit energy at a second bandwidth (e.g., at a second frequency).

Figure 2:
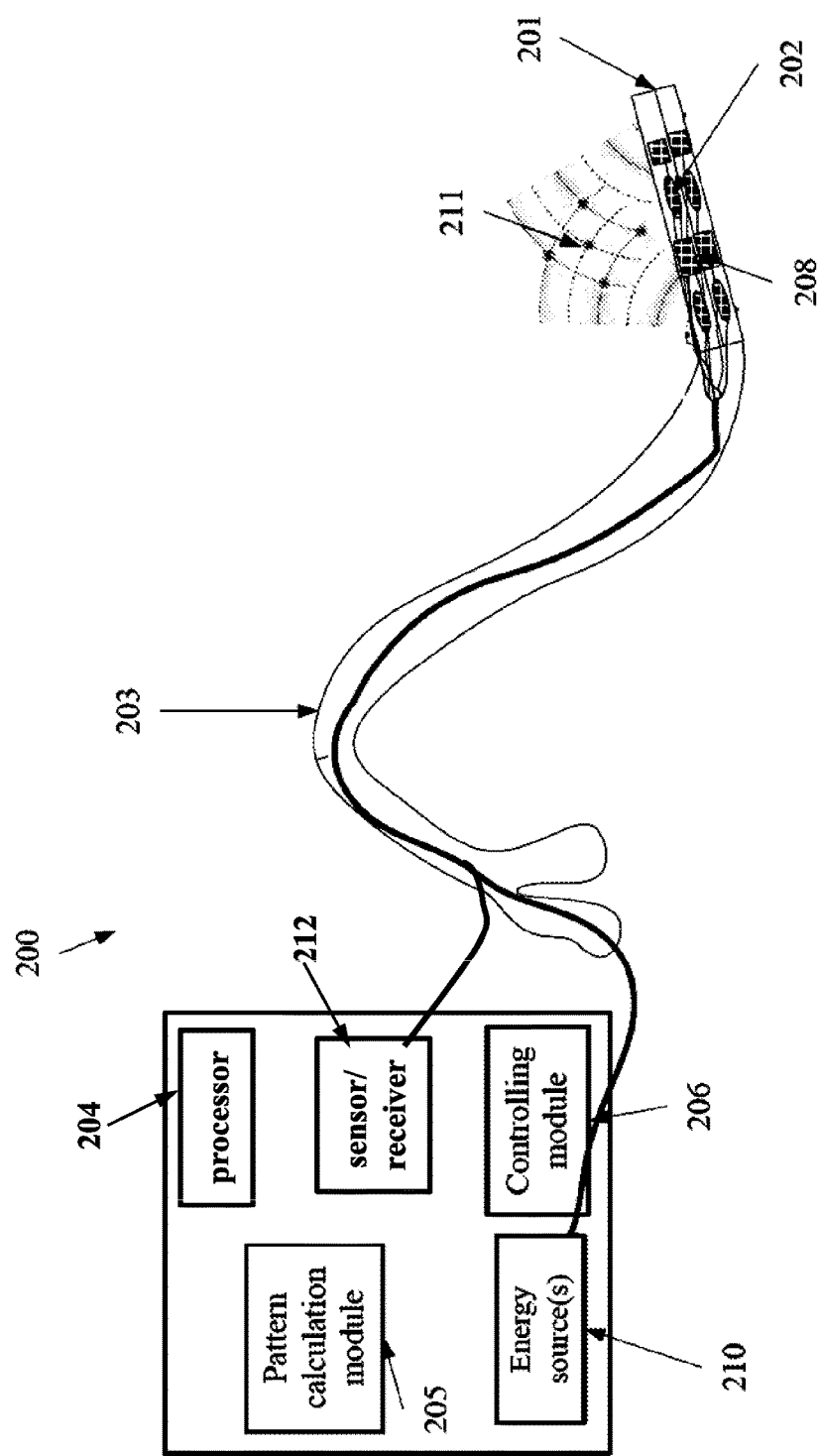
FIG. 2 is a schematic illustration of a system for treating an intrabody tissue, according to some embodiments of the present invention.

Reference is also made to FIG. 2, which is a schematic illustration of a system 200 for treating an intrabody tissue, for example by implementing the method 100 depicted in FIG. 1, according to some embodiments of the present invention. System 200 optionally comprises a processor 204 for calculations and/or control of one or more components of system 200 or multi point probe. Processor 204 may also be configured to receive 105 signal(s) from one or more components of system 200 (e.g., from receiving points).

As used herein, the term "processor" may include an electric circuit that performs a logic operation on input or inputs. For example, such a processor may include one or more integrated circuits, microchips, microcontrollers, microprocessors, all or part of a central processing unit (CPU), graphics processing unit (GPU), digital signal processors (DSP), field-programmable gate array (FPGA) or other circuit suitable for executing instructions or performing logic operations.

The instructions executed by the processor may, for example, be pre-loaded into the processor or may be stored in a separate memory unit such as a RAM, a ROM, a hard disk, an optical disk, a magnetic medium, a flash memory, other permanent, fixed, or volatile memory, or any other mechanism capable of storing instructions for the processor. The processor(s) may be customized for a particular use, or can be configured for general-purpose use and can perform different functions by executing different software.

If more than one processor is employed, all may be of similar construction, or they may be of differing constructions electrically connected or disconnected from each other. They may be separate circuits or integrated in a single circuit. When more than one processor is used, they may be configured to operate independently or collaboratively. They may be coupled electrically, magnetically, optically, acoustically, mechanically or by other means permitting them to interact.

Processor 204 may include and/or connect to, a multi point probe 201 having a plurality of transmission points 202 (e.g., three or more), for example: antennas, radiating elements and/or other transmitting ports. Transmission points 202 (e.g., elliptical elements illustrated in FIG. 2) may be set or otherwise configured to emit simultaneously, concurrently and/or consecutively a plurality of transmission signals, optionally with different frequency, phase, and/or timing Transmitted signal(s) may be modulated signals: e.g., amplitude modulated or frequency modulated. For example, EM energy may be transmitted simultaneously by a plurality of transmission points at the same frequency (e.g., coherent transmission), optionally with a phase difference between two or more transmission points. In some embodiments, EM energy may be transmitted simultaneously by a plurality of transmission points at a different frequency. In some embodiments, EM energy may be transmitted concurrently (at overlapping time intervals) by a plurality of transmission points and the same and/or different frequencies. In some embodiments, the input power (e.g. forward power) provided to the transmission points may be the same and/or fixed throughout the treatment. Optionally, the input power may be adjusted at one or more transmission points throughout the treatment. In some embodiments, frequency and/or phase may be adjusted throughout the treatment. In some embodiments, processor 204 may adjust and/or control the frequency and/or phase and/or input power. Processor 204 may be used for performing all the calculations and/or controlling and/or adjusting described herein.

System 200 may include one or more EM energy sources, such as RF energy sources 210 for providing and/or generating the EM energy (e.g., to one or more transmission points). The source may include one or more of a power supply and/or an oscillator and/or a multiplexor and/or a tuning circuit configured to generate and/or shape electromagnetic waves that carry electromagnetic energy. Optionally, each transmission point 202 is separately connected to the energy sources 210 via one of a plurality of flexible conductive wires, such as waveguide(s) and/or cable(s) placed along a catheter 203. Transmission points 202, and optionally receiving points 208 as described below, may be controlled separately. System 200 may include one or more receiver and/or sensor modules 212. Module 212 may include for example a digitizer and/or a power meter and/or a signal sampler and/or a multiplexor and/or an integrator and/or a counter and/or a bandpass filter and/or a clock and/or a memory and/or a single channel and/or multiple channels and/or a serial port and/or a tuning circuit. Optionally, each receiving point 208 is separately connected to sensor module 212 via one of a plurality of flexible conductive wires, such as waveguide(s) and/or cable(s) placed along catheter 203. Multi point probe 201 is optionally located on and/or in a catheter, such as for example catheter 203, for example at the tip of the catheter 203. Optionally, transmission points 202 are distributed in a plurality of different positions on the tip of catheter 203 and/or on a support structure that is mounted on the catheter 203. As further described below, different support structures, such as balloons, an expendable basket, tent and/or umbrella structure, helical and/or spiral skeletons, branched support and/or any support made of, for example, a shape memory alloy (SMA), such as Nickel titanium (NiTi) may be used. The support structure is optionally designed to expand to deploy points 202 0.5 cm, 1 cm, 2, cm, 4 cm or any intermediate or longer distance from the longitudinal axis of the catheter. The distance between transmission and/or receiving points may range for example between 0.5 and 2 mm and/or between 2 and 8 mm and/or greater than 8 mm. The length of the probe may range between 0.5 and 1 cm and/or between 1 and 4 cm and/or between 4 and 8 cm and/or greater than 8 cm.

In use, catheter 203 may be manipulated via the vascular system of a treated patient to bring multi point probe 201 and/or deploy transmission points 202 and/or receiving points 208 to a proximity with a treatment location, for example a treatment location may include a location of an organ and/or a tissue, for instance as described below. As used herein stating that a probe and/or a transmission point is in proximity to a location may refer to and/or include the probe and/or point being located such that a therapeutically significant part of the transmitted energy reaches and/or passes through the location (e.g., such as at least part of the transmitted energy is absorbed in the tissue). For, example in some embodiments, a transmission point may be said to be in proximity to a location when the distance from the transmission point to the location is less than 2 cm. Alternatively or additional, in some embodiments a bipolar and/or multipolar set of transmission points may be said to be in proximity to a location if a line joining two of the points passes within 2 cm of the location. For example, a probe may be said to be in proximity to a location when a RF signal from the probe is capable of raising the temperature at the location by at least 1-10° C.

System 200 may include a pattern calculation module 205 that is set and/or configured to calculate a multi transmission pattern (also referred here as transmission pattern) defining a respective signal for each of transmission points 202 of multi point probe 201. The transmission pattern may be selected or set to affect one or more selected targets—e.g., one or more regions of the treated tissue. The transmission pattern may form interaction(s) between the respective signals that defines or results in one or more hot spots at the treatment location, for example as shown at location 211. In some embodiments, it may be desired to select a transmission pattern having hot spot(s) that overlap selected targets. The size of each hot spot may vary from less than millimeter via one or more millimeters to centimeter(s), for example, the hot spot is 1 millimeter wide, 2 millimeter wide, 10 millimeter wide or any intermediate size. Controlling the frequency, phase and/or input power at each one or more transmission points may form a specific transmission pattern (e.g., a desired transmission pattern). System 200 may further include a controlling module 206 that instructs one or more power sources (e.g., source 210) to generate transmission signals according to instructions from pattern calculation module 205. In some embodiments, controlling module 206 and/or pattern calculation module 205 may be included or integrated within processor 204.

Optionally, the one or more EM energy sources 210 may include an RF energy generator that provides to each point 202 a power, optionally at a frequency and/or phase, based on instructions from pattern calculation module 205, for example in different phase independent channels. The RF energy generator may have different duty cycles and may be set to generate transmission signals that form one or both treatment signals and/or test signals, optionally interchangeably and/or simultaneously and/or concurrently and/or at different times from different transmission points. Optionally test signals may be recognized at a receiving point based on correlation to a known pattern. Optionally, different transmission points 202 may intercept energy from similar or different sources, for example similar or different RF generators. Optionally, the one or more EM energy sources 210 may include one or more feedback receivers or sensors that measure input power, reflected power and/or temperature and/or impedance of one or more of the points, for example antennas. The feedback receivers may be used to synchronize and/or stabilize the transmission. In some embodiments, the feedback receivers may be the transmission points 202 acting as receiving points 208 (e.g., one or more power meters may be provided to detect input and/or reflected power).

In some embodiments, one or more of the transmission points may be used for measuring impedance (e.g., impedance may be measured between two transmission points). Optionally impedance may be measured prior to and/or during a treatment. Optionally, the impedance(s) measured by the feedback sensors and/or receiver(s) through the antenna(s) is correlated as absolute value(s) (of impedance) at given frequencies. Optionally, these values are complex values. Each complex value includes real and imaginary parts of respective impedance at one of a plurality of different frequencies from one of a plurality of different locations of one of a plurality of transmission points. Optionally, the impedance(s) are used for designing the transmission pattern to affect one or more selected targets. In some embodiments, energy transmission (e.g., for treatment) or transmission pattern is selected in accordance with or based on the measured impedance. Optionally, a modulated signal may be transmitted. Feedback from the modulated signal may be measured (for example using sensors and/or receiving points 208). Based on the modulation of the transmitted signal and the properties (for example the impedance, reflected power, absorbed power and/or their time dependence) of the feedback, dielectric properties of the treatment area may optionally be calculated (for example by inverse modeling). For example, based on the modulated transmission signal and the measured feedback, a treatment pattern may be selected.

According to some embodiments, a forward model of the transmission signals may be calculated for treating a target in a treatment location. The model may define a set of transmitted signals which is selected based on the reception of one or more test signals to treat a selected target and/or a set of expected consequences. The test signals may be intercepted by receiving points 208 which may be located on the multi point probe and/or on an external supporting device which is not on catheter 203, for example a patch set to be located on the back of the treated patient and/or a transmitter in the room. As used herein the term forward model may refer to and/or include a preliminary pattern of transmitted signals, a pattern of test signals, one or more predicted outcomes and/or one or more respective response transmission patterns. For example the preliminary pattern of transmission signals may optionally be transmitted to the tissue. The pattern of test signals may be measured during and/or after transmission of the preliminary pattern. A response pattern may be selected corresponding to a predicted outcome that most closely matches the measured test pattern. Optionally, the test pattern and/or the response pattern may be modified in accordance with the measured test outcome.

According to some embodiments of the present invention, multi point probe 201 may include one or more receiving points 208 which are set to intercept RF energy transmissions. Optionally, receiving point 208 is also a transmission point 202, for example an antenna. In use, data received from one or more receiving points 208 may be used for calculating dielectric properties tissues in the treatment location (e.g., to obtain a map of dielectric properties). The calculation is optionally performed by the pattern calculation module 205. For clarity, a dielectric property of tissue describes an interaction of the tissue with EM field(s) and may be represented by a frequency dependent complex number describing electrical permittivity and conductivity of the material, for example as known in the art. It should be noted that different human tissues are characterized by different dielectric properties. Such dielectric properties has an effect on electro-magnetic radiation that is transmitted to and/or reflected from the related tissue, for example: changes the attenuation of the transmission and/or reflection, changes a delay that is caused by the tissue, changes a phase of the transmission and/or the reflection, or changes the dispersion of the radiation in the related tissue. Optionally, the data received from receiving points 208 is used, for example by the pattern calculation module 205, to calculate the transmission pattern in light of the dielectric properties of the tissues in the treatment location. For example, pattern calculation module 205 may set transmission pattern(s) by selecting one or more pre-stored transmission pattern, e.g., transmission patterns may be selected from a look-up table based on data received from receiving points 208 (e.g., based on a map of dielectric properties).

Optionally, dielectric properties and/or changes in dielectric properties over time and/or changes in dielectric properties in response to transmitted signals, and/or dependence of dielectric properties on signal frequency may be correlated with tissue type and/or tissue properties such as for example water content, density, heat capacity and/or blood perfusion.

Exemplary embodiments, system 200 may be used for neural ablation, for example for renal denervation. In some embodiments, multi point probe 201 may radiate a treatment location with EM energy, e.g., RF energy, simultaneously, concurrently and/or at different times from a plurality of transmission points located at the tip of a catheter that is guided toward the treatment location (e.g., renal artery). Catheter 203 may be guided and/or transmissions points may be deployed in the vasculature adjacent to a target neural site using standard interventional catheter techniques. RF energy may then be delivered through transmission points 202 to the treatment location that includes target nerve(s). In some embodiments, receiving points 208 may be placed on the catheter 203, for example on the tip thereof.

In some embodiments, system 200 may be designed for carotid body selective ablation. The carotid body has many different nerves going therethrough where each fiber has a different dielectric property. System 200 may enable selecting a target property range and ablating nerves within the range. This feature of selective ablation of tissue within a target may be enabled by signals or transmission pattern selected such that they affect a target with certain dielectric properties and not other. The differentiating properties may be ionic strength, fat content and/or the dimensions of the fiber(s).

In some embodiments the pattern may be selected to increase interaction between signals for a particular tissue (i.e. a target) and/or to decrease interaction for another tissue. Optionally the interaction may be spatial. For example, a target (e.g. a carotid body) may be ablated by applying energy along multiple paths that intersect at the target location. Optionally, a pattern may be selected wherein a combined signal along the multiple paths may ablate the carotid tissue, while on each path, the chosen signal properties may protect the intervening tissue. For example, a first path may be chosen where the map indicates tissue that is relatively more conductive at 1 GHz (for example possibly nerve tissue) and a second path where the map indicates tissue more relatively more conductive at 10 GHz (for example possibly vascular tissue).

Optionally, the frequency of the ablation signal between a first pair of electrodes across the first path may be chosen in the 1 GHz range and/or the frequency of the ablation signal between a second pair of electrodes across the second path may be chosen in the 10 GHz range. The two signals may be selected having a frequency and/or phase that produce constructive interaction (e.g. resonance) at the location of the target. Optionally, the interaction may be temporal. For example the timing of the pattern may be chosen to produce more interaction in one tissue (e.g. a target) and less interaction in another tissue. For example, the timing may be selected to ablate the carotid body but not the intervening tissue. For example, a signal may be applied at higher energy and/or for longer bursts along the second path where high blood perfusion (and/or heat advection) may protect the intervening tissue more. For example, a signal may be applied at lower energy and/or shorter bursts along the second path where low blood perfusion (and/or low heat advection) may protect the intervening tissue less. The timing of the pattern may optionally be chosen to produce more interaction in one location (e.g. a target) and less interaction in another location. For example, to ablate a region insulated by fat but not the intervening tissue. For example, a signal may be applied at lower energy and/or with long breaks to ablate an area insulated by fat. For a target with low blood profusion (for example fat) short signals with long waiting periods may optionally be chosen (due to low blood profusion, heat may remain in the tissue and signals may interact over longer time periods). For example, an interruption may be used between sequential transmissions. The length of the interruption may be selected to allow heat to dissipate from healthy tissue with high blood perfusion and/or high heat dissipation, but to build up heat in cancerous tissue with poor blood perfusion and/or low heat dissipation. The heat buildup may destroy cancerous tissue while healthy tissue remains intact. Optionally a database of lookup table of tissue properties and/or ablation patterns may be supplied. The database may include patters to avoid one tissue and/or to focus on another tissue.

In some embodiments a pattern may be selected to increase interaction with a certain chemical. For example, a first ablation may tuned (with a specific wavelength) that affects a chemical (either a naturally occurring chemical or a chemical marker, for example bound to an antibody). A later ablation may be tuned to affect a product of the interaction of the first ablation and the chemical. Optionally, a database and/or a lookup table of chemical properties and ablation patterns may be provided. The database may include patters to avoid one chemical and/or to focus on another chemical. For example, microwave frequencies may be used to heat water.

In some embodiments consecutive transmissions may interact with a single target and/or tissue. Interactions with different tissue may have different time kinetics for example, interactions may be related to the interaction of the transmitted wave and the properties of the tissue and well as the spatial/time/dynamic properties of the tissue (e.g. dielectric properties, blood flow serving as a heat sink and many more perturbations including those that can be introduced temporarily such as ligands, antibodies, markers, and/or tracers). The lasting effect of a transmission may be referred to as tissue "memory". A subsequent transmission may interact with the changes brought about by a previous signal to generate a therapeutic effect. The interaction with the target may differ between a target tissue and a non-target tissue. For example, the consecutive transmissions may ablate the target tissue while doing limited or no damage to other tissue.

Reference is now made, once again, to FIG. 1. First, as shown at 101, a treatment location in a body of a treated patient may be selected. For example, the treatment location may include one or more nerves for ablation and/or a fat tissue to remove in a lipolysis procedure and/or muscle tissue. Optionally, the treatment location may be relatively accurately selected using an imaging modality, such as ultrasound, CT, magnetic resonance imaging (MRI), and/or any catheterization laboratory (Cath lab) imaging equipment used to support the catheterization procedure. The imaging (including the methodologies listed above) may optionally be performed in an extrabody modality, for example using imaging sensors and/or transmitters located outside the body of the patient. Alternatively or additionally the imaging (including the methodologies listed above) may optionally be performed in an intrabody modality, for example using imaging sensors and/or transmitters located inside the body of the patient.

Optionally, the user (e.g., a physician) may define and/or select a target tissue and/or a depth of penetration from the location of probe 201. The defining and/or selecting are optionally performed using a graphical user interface (GUI). Optionally, the selection and/or definition is indicative of one or more dielectric properties of a target area (as tissues are made of different composite of components such as water electrolytes, fat and protein, different tissues have different properties, for example neural tissue is known to have high fat content.

Now, as shown at 102, during a medical or cosmetic procedure, a multi point probe that has a plurality transmission points (e.g., three or more), such as probe 201, may be maneuvered to proximity with the selected treatment location in the body of the patient. The maneuvering is optionally performed using a catheter, such as catheter 203, which may be guided using an imaging modality, such as the above mentioned imaging modalities. Optionally, the guiding is performed using an optical fiber and/or other imaging sensor (s) located on the tip of the catheter, for example as known in the art. Optionally, multi point probe 201 is brought to a close proximity with the treatment location, for example to less than 2 centimeter (CM) from the treatment location. For example, multi point probe 201 may be maneuvered in a blood vessel to deliver RF energy via one of the walls of the blood vessel toward a part of an organ, for example via the renal arteries toward a renal nerve during a renal denervation process. Optionally, transmission points 202 are deployed in a blood vessel to be in touch with the walls of the blood vessel. Such a deployment may be performed, for example as outlined above and described below with reference to FIGS. 4-8.

As described above, probe 201 of system 200 may include one or more receiving points 208. In some embodiments, receiving points 208, which are optionally antennas, are used for sensing and optionally imaging the volume in proximity to probe 201, for example to make a map of dielectric properties. In some embodiments, receiving points 208 may be used for guiding the probe toward a treatment location.

As shown at 103, and optionally after probe 201 is located in proximity to the treatment location, a transmission pattern may be calculated or otherwise set, for example by the pattern calculation module 205 and/or selected from a database of predefined patterns. Transmission pattern may define, for each point of a plurality of (e.g., for each) transmission points, a respective signal of a plurality of transmission signals. For example, transmission pattern may define the frequency, phase, timing and/or input power of the respective signals provided to the transmission point(s). The transmission pattern may be set to form an EM field with interaction(s) between respective signals, for example a destructive and optionally constructive interference, defines one or more hot spot(s) at the treatment location. Optionally, the hot spots are created by summing up different waves from different transmission points at a target area (e.g., tissue) and at the same time creating the opposite effect, for example cold spots, on a proximate tissue that is not in the target area. Optionally different respective transmission signals have different phase, frequency and/or modulation.

In some embodiments, processor 204 and/or controlling module 206 may control energy source 210 such that the transmission pattern is transmitted by transmission points 202, for example: processor 204 and/or controlling module 206 may control energy source 210 such that signals at the defined frequency, phase or input power are provided or supplied to the transmission point(s).

Optionally, the transmission pattern is based on data that is acquired in a testing session that is performed using the receiving and transmission points 208/202. Optionally, during an iterative process, transmission points 202 transmit test signals which are intercepted by receiving points 208. For example, in case probe 201 includes a set of antennas, each functions both as a transmission point 202 and as a receiving point 208. Controlling module 206 may instruct feeding each of points 202 (e.g., antennas) separately and optionally sequentially with a transmission feed to allow it to transmit a respective test signal that may be intercepted by the other antennas (the signal may be coupled from the transmitting antenna to other antennas currently not transmitting). Receiving points 208 may intercept the energy from the treatment location and the respective receptions may be analyzed, for example by pattern calculation module 205, e.g., to map dielectric properties of sub volumes in the treatment location. It should be noted, that part of the signal may be reflected back to the transmitting antenna and may also be used in the analysis. The analysis may be based on reception of test signals from each one of the antennas by each of some or all of the other antennas. Transmission points 202 may transmit at different times, for example sequentially, one after the other and/or in different groups that transmit simultaneously and/or concurrently, for example pairs or three transmission points 202 at a time and/or the like. Optionally, during the analysis a set of equations that is based on a relationship between intercepted and transmitted energy is optionally solved. This relationship is indicative of energy absorbed by the tissue(s) located in the treatment location.

Optionally, based on this relationship the transmission pattern is set. For example, different tissues have different dielectric properties and therefore expected to cause RF energy to travel differently in the treatment location. The route of the RF energy is optionally induced from an analysis of the strength of test signals as captured by different receiving points 208 which are located in different positions in relation to the treatment location. For example, fat has a higher resistance to the flow of RF current than muscle and water. This dielectric property causes RF energy to route, where available, via alternate lower resistance routes. When such an RF energy routing is discovered by an analysis of the readings of the different receiving points 208, a transmission pattern with hotspot(s) on neural tissue(s) (which have high fat content) may be calculated. It should be noted that in this example, hot spot(s) are formed on target tissue(s) which are less conductive than the surrounding tissue(s), for example by controlling interaction(s) between co-transmitted signals in the respective EM field.

Optionally, the RF energy intercepted by receiving points 208 may allow generating a three dimensional (3D) volumetric map of the dielectric properties of the tissues in the treatment location and/or therearound. The map of the dielectric properties is optionally rendered to the operator of system 200, for example presented on a display.

Optionally, the map of the dielectric properties is combined with an anatomical map of the treatment location and optionally of the surrounding. For example, the anatomical map is acquired by an imaging modality, such as ultrasound CT, magnetic resonance imaging (MRI), and/or any catheterization laboratory (Cath lab) imaging equipment used to support the catheterization procedure in real time. In another example, the anatomical map is acquired from a database, for example selected by a user and/or selected according to the type of the procedure. The anatomical map may be represented as one or more 3D matrices of coefficients each indicative of a value of certain dielectric property. This combination is optionally presented to a user, allowing the user to specify a location of a target area (e.g., tissue) as well as indicating by the selection characteristics of the target area.

The transmission pattern is optionally a set of instructions calculated to instruct feeding the transmission points with of a plurality of transmission signals. The transmission pattern optionally defines the frequency, phase, modulation, transmission timing and/or period of each one of the transmission signals. The transmission pattern may be a temporal pattern—for example: it may include a set of instructions for delivering energy (e.g. transmitting a signals) from each of the transmission points with a respective signal(s) and the timing of such feeding. In some embodiment, a summing of such transmission signal(s)—e.g., the corresponding EM fields created as a result of such consecutive transmission— may define one or more hot spots at the treatment location— thus in the aggregate: this may results in ablating a desired target. In some embodiments, transmission pattern may include a transmitting schedule, the transmitting schedule may comprise timing instructions for transmitting from the transmission points at different times with the transmission signal(s) and the frequency, phase or input power of such signal(s). In some embodiments, transmission pattern may include instructions to intermit transmitting (for example a transmitting event may last between 5 and 20 seconds and/or between 20 and 120 seconds and/or between 120 and 600 seconds). between two transmitting events, e.g., it may instruct to interrupt radiation for 1, 2, 3 or more seconds. In some embodiments, intermission durations may be determined based on data received from receiving points, e.g., during the treatment process. In some embodiments, transmission pattern may include instructions to feed a sub set of the transmission points. In some embodiments, transmission pattern may include instructions to feed a first sub set of the transmission points for a first period and then to feed a second sub set of the transmission points for a second period. In some embodiments, the first and second sub set of transmission points may be selected based on data received from receiving points, e.g., during the treatment process. The power of a transmission may optionally range for example between 1 and 3 watts and/or between 3 and 7 watts and/or between 7 and 12 watts or may be greater than 12 watts.

A transmission pattern may allow forming a desired EM field with interaction(s) between co-transmitted respective signals that define one or more hot spots at the treatment location, for example by forming an EM field with destructive and/or optionally constructive interference. The hot spots are optionally created around and/or on one or more ganglions of nerve cell bodies in a target area. For example, the hot spots may be set to ablate by heat the fat in a neural tissue that surrounds ganglions inducing the ablation by heat of the ganglions themselves.

In some embodiment, the location of fat tissue in or around the treatment may be detected. For example, the transmission pattern may be set for treating Ganglia around pulmonary veins (PG) which are fat structures embedded in fat tissue with a diameter of 2-3 CM and are considered as part of the reason for atrial fibrillation sustainment. It should be noted that this allows using RF energy to ablate nerves even though the Ganglia are made of high percentage of fat and the RF energy is naturally not conducted well through fat as it rather flow via polar tissues adjacent to the fat, for example via blood and/or intracellular fluids. A transmission pattern may be selected to ablate the fat and/or to bypass the fat and ablate other tissue.

As shown at 104, after the transmission pattern is calculated, plurality of transmission signals may be simultaneously and/or concurrently and/or consecutively transmitted (e.g., according to a pattern and/or at different times according to feeding schedule) from the plurality of transmission points onto the treatment location according to the transmission pattern.

Figure 3:
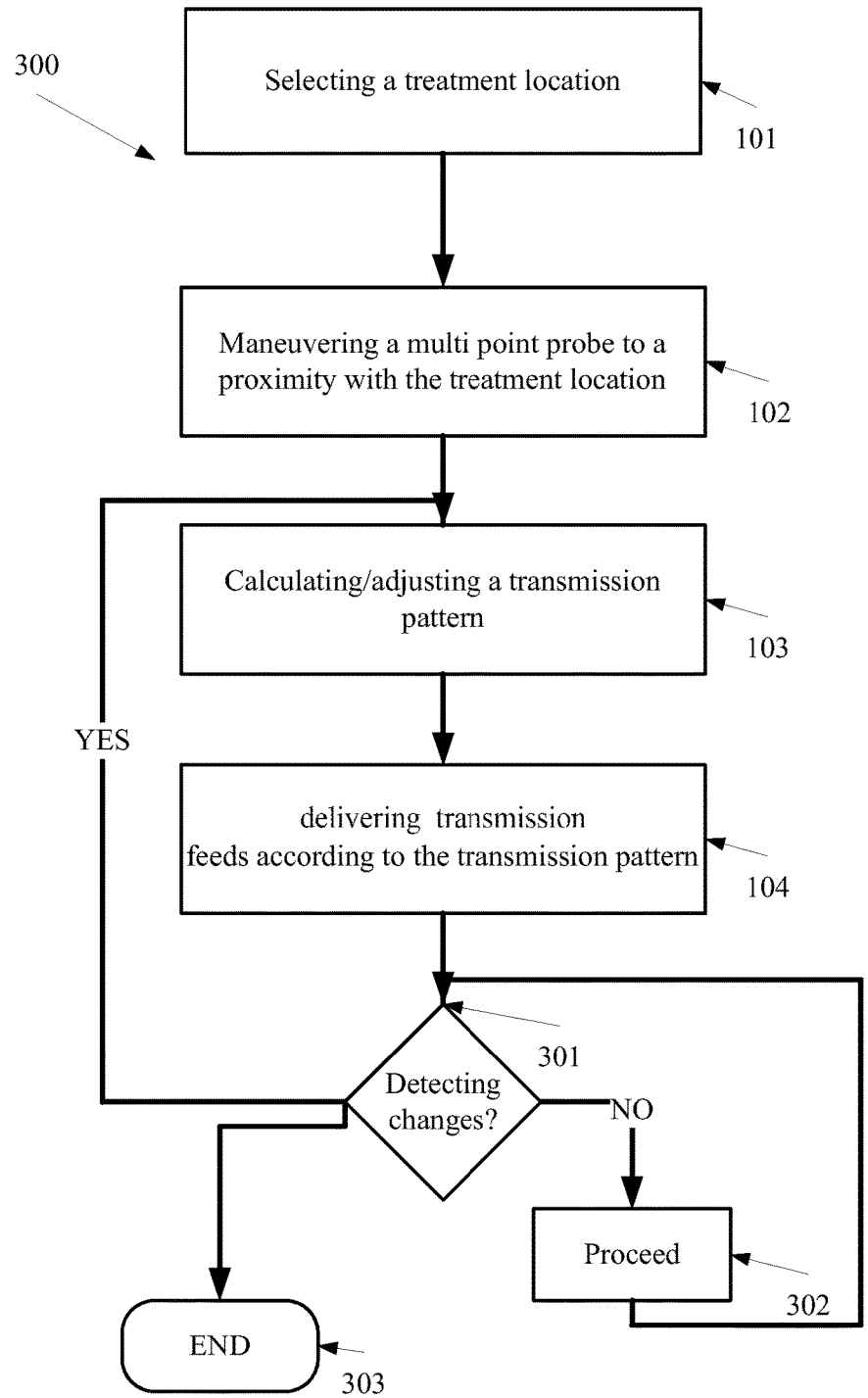
FIG. 3 a flowchart of a method of treating an intrabody tissue, according to some embodiments of the present invention.

Reference is now made to FIG. 3, which is a flowchart of a method 300 of treating an intrabody tissue, according to some embodiments of the present invention. Method 300 may include forming a dynamic EM field with interaction(s) between respective co-transmitted signals by adjusting a transmission of respective signals from a plurality of transmission points. 100-104 are as depicted in FIG. 1; however FIG. 3 further depicts 301-302 which may allow dynamic adjustment of the EM field during a medical treatment. The transmission pattern may be adjusted when real time changes in the dielectric properties of the tissues in and/or around the treatment area are detected (e.g., when a change in the map of dielectric properties of a treatment location is detected). In some embodiment, the actual change in dielectric properties may not be detected but rather a change is detected in the data received from receiving points. As described above, multi point probe 201 may include receiving points 208. Optionally, the dielectric properties of tissues of the treatment area or the area therearound may be monitored during the transmission of the transmission signals, for example according to an analysis of the reading of receiving points 208, also referred to herein as a feedback. At 301 changes may be detected (e.g., changes in dielectric properties of the treating area). If a change in one or more of the dielectric properties is detected above a certain threshold and/or not detected above a different threshold, the transmission may be automatically adapted, for example increased, changed (e.g., in frequency and/or phase), decreased, modulated and/or otherwise adjusted. For example, as depicted in FIG. 3, the transmission pattern may be recalculated and/or adapted according to the detected changes. As shown at 302, if no change is detected, energy delivery may continue (e.g., according to the current transmission pattern). As shown at 303, energy delivery may automatically and/or manually end, for example when the detected change is indicative of a desired outcome and/or an undesired outcome of the energy delivery process. Optionally, the decision whether to proceed with the energy delivery process and/or whether to increase, change, and/or decrease the transmission of one or more of the transmission points may be based on matching with pattern templates, optionally predefined.

According to some embodiments of the present invention, the above described system 200 may be used for generating a map of dielectric properties of a treatment location using multi point probe (for example: probe 201) with optionally receiving points 208, e.g., to obtain or calculate a map of dielectric properties a treatment location—which may be referred herein as dielectric map. This map may be optionally presented to a system operator, for example as described above. In use, after the multi point probe is brought to proximity with the intrabody treatment location, for example as outlined above and described below, signals may be transmitted and intercepted (for example by intercepting energy) by transmission and receiving points 202, 208. The dielectric map may be generated by a set of equations that is based on the relationship between the intercepted and transmitted energy in the signals, for example as described above. Optionally, the dielectric map may be presented on a display of the system, allowing the system operator to select tissues for therapy and/or ablation. For example, the system operator may select the type of tissue to ablate and/or treat, for example from muscle, blood, fat, and/or the like. Optionally, the dielectric map allows the system operator to identify the tissues. The identification may be used for identifying typical dielectric properties of the tissues. Optionally, as described above, the dielectric may be merged with an anatomical map of the treatment location to obtain a combined image. For example, the dielectric map may be presented as a layout on top of the anatomical map. For example the resulting map may be used to determine the location of fat and/or other tissue and/or substances (for example oils, proteins, lipids, and/or minerals) in the treatment location.

Optionally, the treated patient may be injected with artificial dielectrics which are selected to mark specific target tissue(s) and/or substances, for example artificial dielectrics connected to antibodies targeted to nerve cells. During the process, the artificial dielectrics may be used to direct the energy to the marked target tissue. In some embodiments an artificial dielectric may include metal particles in a liquid form and/or formed into a solid (for example solidified foam). The artificial dielectric may optionally be positioned (for example via injection and/or using a catheter). The artificial dielectric may optionally serve as a lens focusing and/or scattering a signal.

Reference is now made to FIGS. 4-8 which are schematic illustrations of different structures for supporting a plurality of transmission points 202 and optionally a plurality of receiving points 208, referred to herein interchangeably and/or as antennas, according to some embodiments of the present invention. The supporting structure is optionally set to be mounted on the tip of a catheter (e.g., catheter 203). Optionally, the supporting structure has a compressed state when it is located in a lumen of the catheter when conducted toward the treatment location and a deployed state when it is extracted from the catheter.

Figure 4:
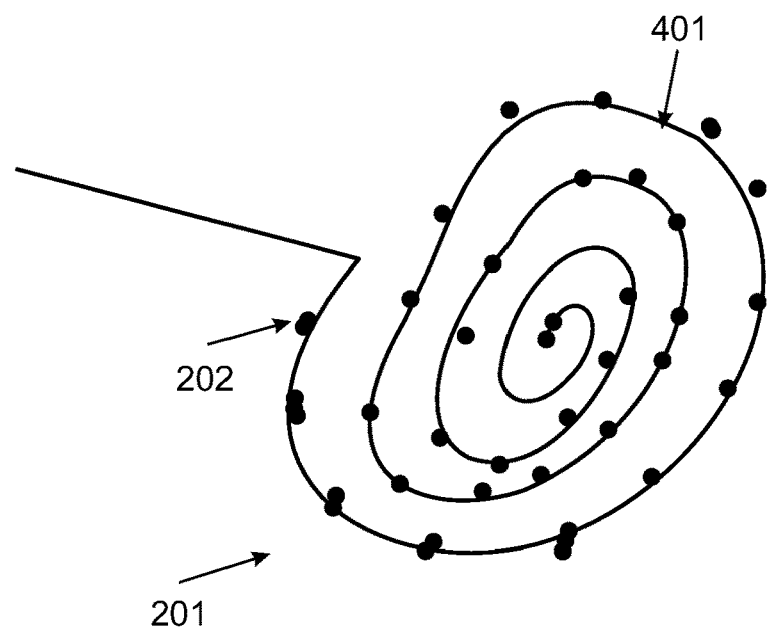
FIGS. 4-8 are schematic illustrations of different structures for supporting a plurality of antennas, according to some embodiments of the present invention.

In FIG. 4 the supporting structure has a spiral structure. This structure may allow or facilitate locating the antennas (for example transmission points 202 and/or receiving points 208) in different distances and/or angles from a common center, for example at the time of a spiral structure 401 which is optionally made of SMA. A helical structure may also be used so as to place antennas (for example transmission points 202 and/or receiving points 208) in direct contact with the blood vessel walls.

Figure 5:
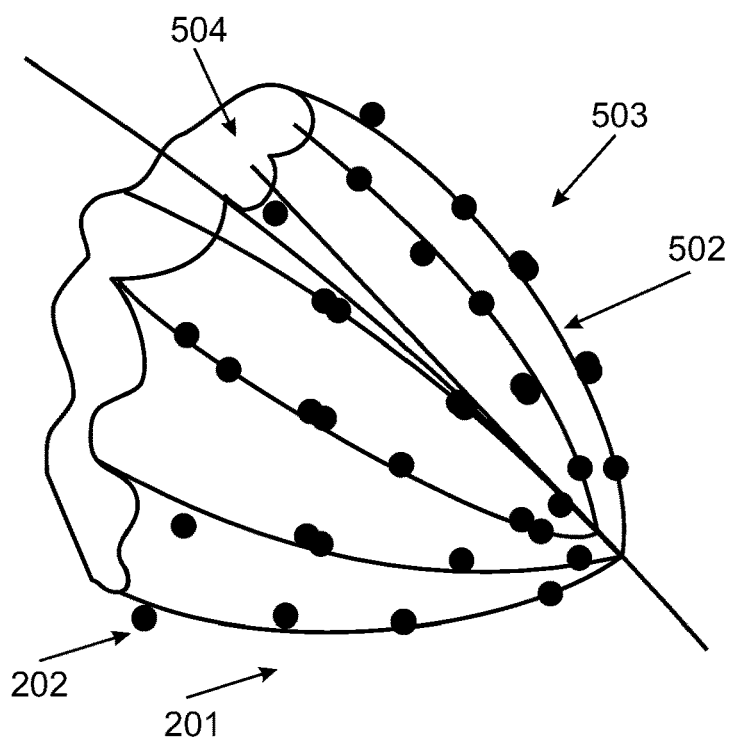

In FIG. 5 the supporting structure includes a plurality of branches, such as 502, which are curved on top a virtual hemisphere 503. This structure may allow locating the 0020 transmission points 202 in different distances and/or angles from a common center, for example at the time of a spiral structure 401 which is optionally made of SMA. In some embodiments, some or all of the antennas may be placed around a treatment area, for example around spleen 504. The supporting structure may include for example ribs and/or stretchers (e.g., like an umbrella and/or other support (e.g., brace, buttress, stanchion, cantilever, strut, frame and/or spines). The supports may include, for example, inflatable supports, supports made of nitinol, a folding basket, a slit straw structure, a stent, a folding stent, and/or an expandable woven structure. It should be noted, that each branch (e.g., branch 502) may be provided with different numbers of antennas, having a similar or different distance between two or more antennas.

Figure 6:
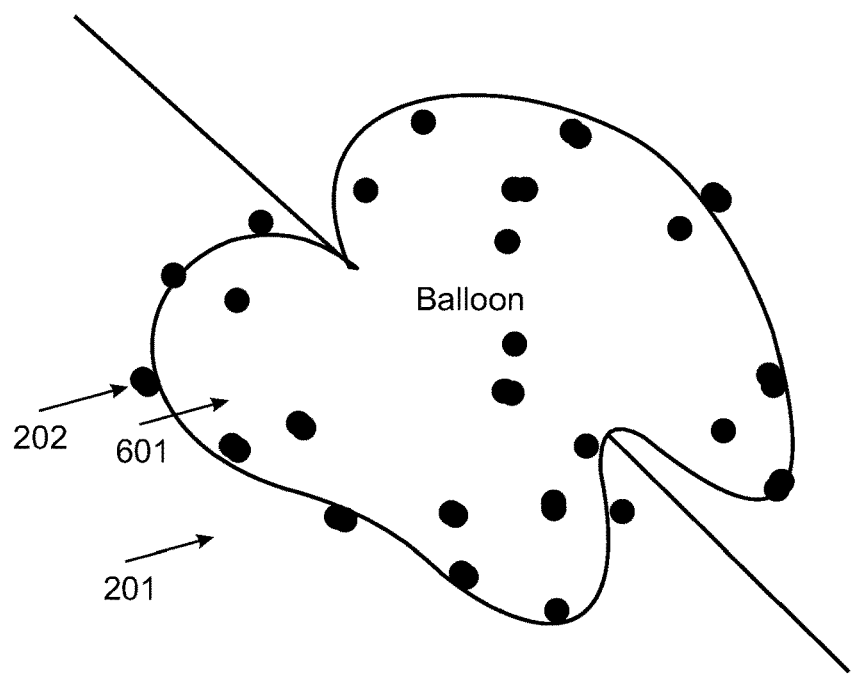

In FIG. 6 the supporting structure is inflatable and/or mounted to be expended by an inflatable body, such as a balloon 601. This structure may allow deploying antennas (for example transmission points 202 and/or receiving points 208) away from one another in the deployment state by inflating the inflatable body. In some embodiments, antennas (for example transmission points 202 and/or receiving points 208) may be brought to contact with walls of a blood vessel and/or another intrabody lumen. The inflatable body may deploy antennas toward the walls of the lumen regardless of its width and/or shape.

Figure 7:
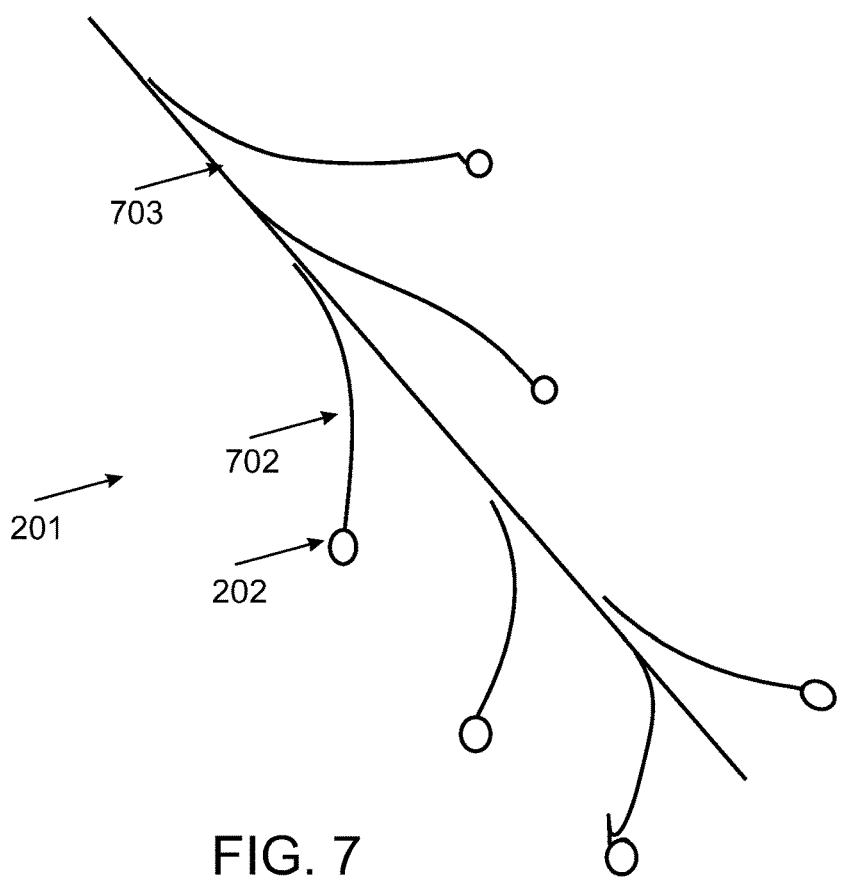
Figure 8:
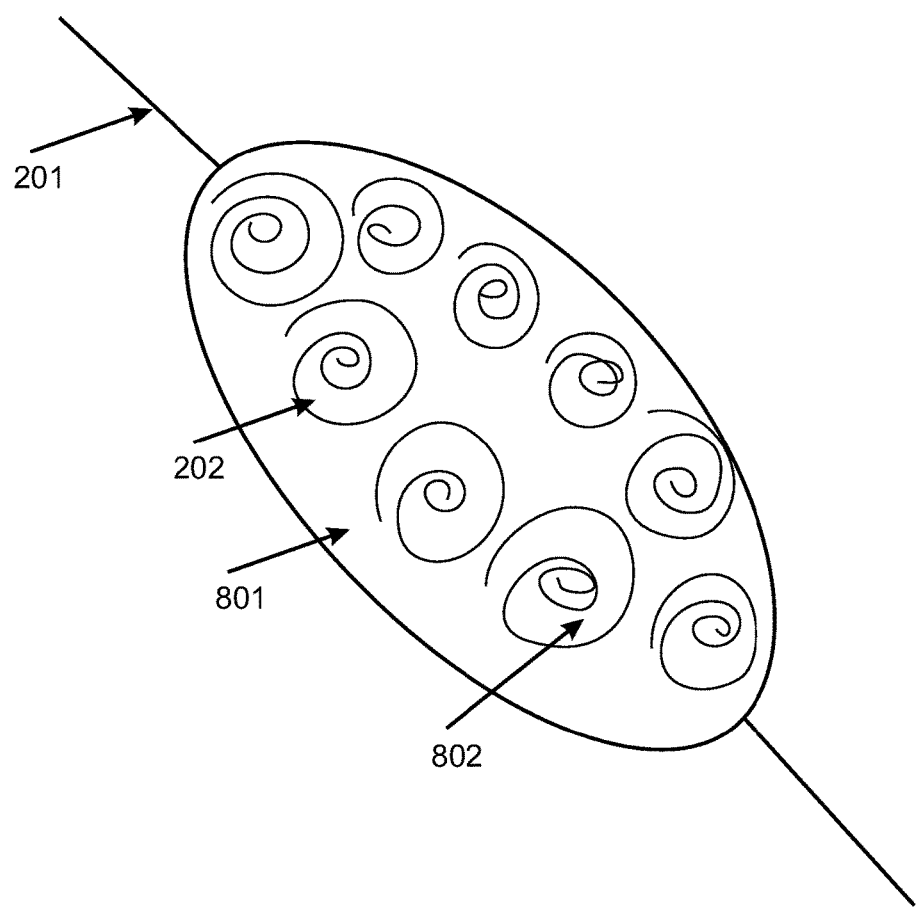

In FIG. 7 the supporting structure includes a plurality of branches, such as 702, which are branched out of a supporting stem 703. This structure may allow locating antennas 802 (for example transmission points 202 and/or receiving points 208) in different distances along a blood vessel and/or another intrabody lumen. In some embodiments, some or all of antennas 802 may be placed in contact with the walls of the respective intrabody lumen. In FIG. 8 the supporting structure is an oblong body 801 that supports a plurality of arrays of antennas 802. This structure may allow locating a number of spiral arrays of antennas 802 in different distances along a blood vessel and/or another intrabody lumen. In some embodiments, some or all of antennas 802 may be placed in contact with the walls of the respective intrabody lumen.

In some embodiments, a multipoint probe may contain a plurality of wires. The wires may join one or more antennas (for example antennas 802), including for example transmission points (for example points 202) and/or receiving points (for example points 208) to a signal generator and/or receiver. A separate respective signal may be sent and/or intercepted to each single and/or group of antennas via the respective wire. For example, the multiple wires may run from a plurality of signal generators and/or power meters and/or from a single generator and/or power meter connected to a multiplexer. The wires may run through a catheter to the multipoint probe. For example in the branched structure (for example as illustrated in FIGS. 5 and/or 7) a wire may run up each branch. For example in a serial structure (for example as illustrated in FIG. 4) a bundle of wires may run along the line of points each point and/or set of points connected to a respective wire.

Figure 9:
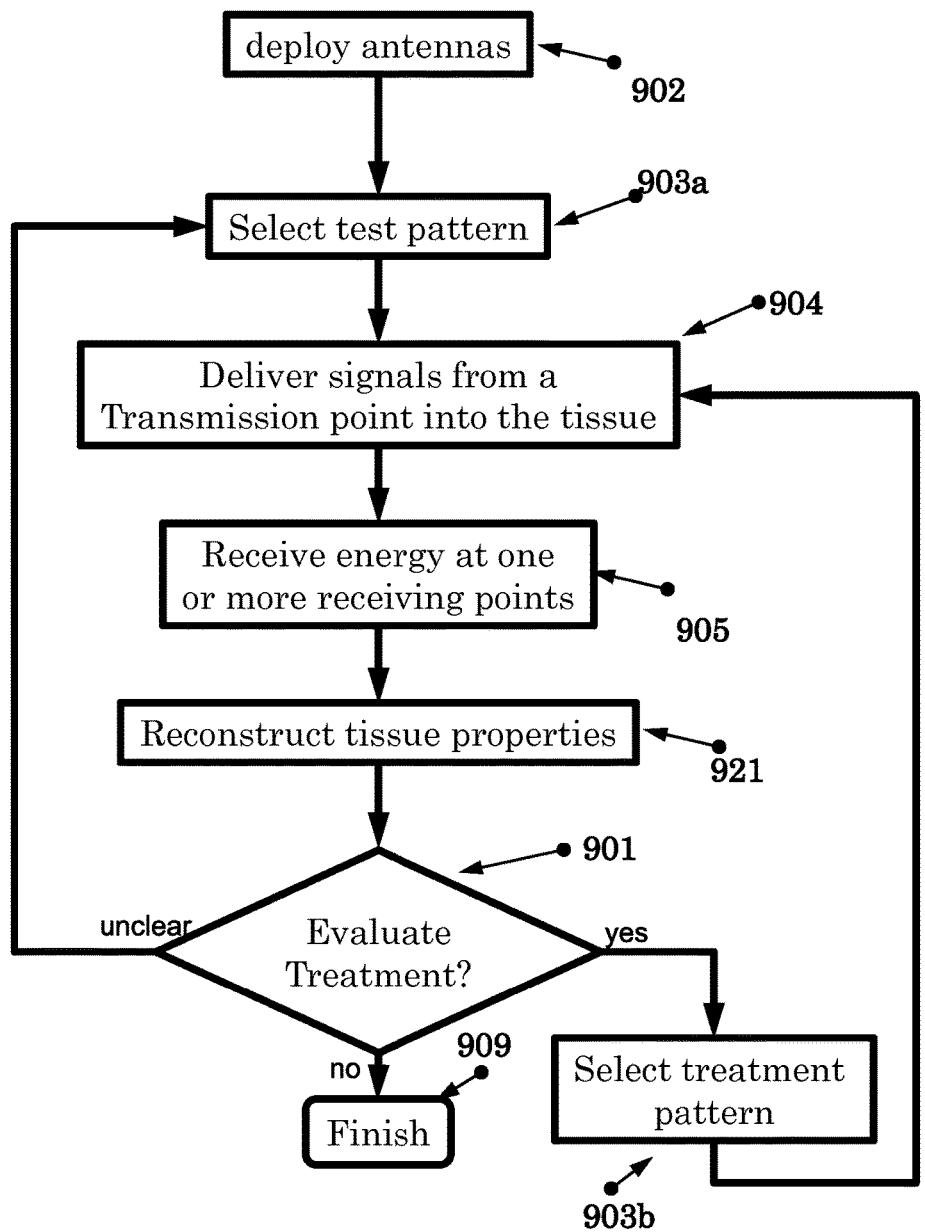
FIG. 9 is a flow chart illustrating of a method of intrabody imaging according to some embodiments of the present invention.

Reference is now made to FIG. 9 which is a flowchart illustration of a method for intrabody imaging according to some embodiments of the current invention. The method may include selecting 903a and/or delivering 904 a test pattern transmission from one or more transmission points of a multipoint probe. The test pattern may interact with tissue in a test area (for example in or around a treatment area). The resulting energy may be intercepted 905 at one or more receiving points. Optionally tissue properties may be reconstructed 921 based on knowledge of the intercepted 905 energy and/or the transmitted energy. A decision may be made whether to treat 901 the treatment area and/or make further tests and/or finish 909.

In some embodiments, a multipoint probe may be maneuvered 102 to a proximity with the treatment location for example as described above with respect to FIG. 1. Optionally, maneuvering 102 the probe may include inserting the probe including and/or deploying antennas 902 including transmissions points and/or receiving points (for example transmission points 202 and/or receiving points 208) to a position in proximity of a treatment area. For example, a multipoint probe may include embodiments as described above (e.g. FIGS. 2 and/or 4 to 8).

In some embodiments a test pattern may be selected 903a. For example, the pattern may include signals that are delivered 904 simultaneously and/or concurrently and/or consecutively. One or more signals may be delivered 904 from a single transmission point and/or from multiple points. For example, two signals having different properties may be delivered 904 one after the other between two transmission points.

Optionally there may be a delay between transmissions delivered 904 at different times. The interaction between the signal and the tissue (for example impedance, induced change in temperature, reflected signals, absorbed energy) may be measured for the different signals and/or times by for example a sensor (e.g. a power meter and/or a receiver for example. A sensor may optionally detect signal properties (e.g. wavelength, phase, power). The result may optionally be used to deduce dielectric and/or physical properties and/or geometry and/or content of the tissue. For example a reverse problem may be solved to determine which tissue structure and/or dielectric structure could produce the measured signals under the known input single pattern. The solution could optionally be conditioned on known tissue structures (for example measured using extrabody imaging) and/or known constraints on the physiology and/or anatomy of the patient.

In some embodiments, one or more respective signals may be transmitted along different transmission paths. For example, a one dimensional, two dimension and/or a three dimensional map may be made of the test area (e.g. as described above). In some embodiments, intrabody mapping may be used in conjunction with extrabody imaging (for example as described above). For example, measured dielectric properties of a region (based on intrabody mapping) may be correlated with structures measured using an extrabody modality (for example x-rays, ultrasound, CT, MRI) to identify structures.

In some embodiments, the results of the mapping may be used to decide whether to proceed with a treatment 901. Alternatively or additionally, the measured energies may be used directly for decide whether and how to proceed with a treatment 901 and/or further testing, for example without reconstructing a map. For example, a mapping may indicate the presence of a target for ablations, for example nerve tissue and/or a fat body. The map may for example also indicate the presence of a confounding structure, for example a low inductance structure blocking an energy path and/or a sensitive structure that may be harmed in by the treatment. For example, a processor may determine if there is an effective transmission pattern that can be expected to treat the target without causing undue harm to other structures. For example various possible treatment options and/or patterns, their risk and/or their probability of success, may be evaluated. If there is, for example, no pattern with acceptable risk and probability of success, the process may end 909 and a new location for ablation and/or a different treatment may be sought. If there remains a high level of uncertainty, for example, a new test pattern may be selected 903a and an improved map may be produced to reduce the uncertainty. Evaluation may include comparing measured energies and/or computed maps to a look up table and/or database of.

In some embodiments, a treatment pattern may be selected 903b (for example as described herein above) and delivered 904. For example the selected treatment pattern may be a treatment pattern with acceptable prognosis (acceptable risk and probability of success). During and/or after treatment energy may be intercepted 905 at receiving points. The intercepted 905 energy may be used as feedback to analyze progress of treatment and/or to reconstruct 921 the map of tissue properties. Based on the updated information, the treatment may be reevaluated 901.

In some embodiments, after producing a dielectric map in one location, the probe may be moved and a dielectric map produced in a second location. The processor may store the first dielectric map, identify the movement of the probe and compute second dielectric map taken into account the first dielectric map. For example known values of the first dielectric map may be taken as constraints to solving the inverse problem at the second location. Alternatively or additionally, a dielectric map may be reconstructed using a model and/or image and/or a lookup table and/or a database (for example from an extrabody imaging modality and/or a physiological based model) as a starting point for solving the inverse problem. Alternatively or additionally, a second dielectric map may be reconstructed at a later time and/or a different location using a previously computed map as a starting point for an optimization procedure solving the inverse problem.

It should be noted that the present invention is not limited to antennas of similar structure or function and that the plurality of antennas may be of different geometry shape, material, size etc. The plurality of antennas may be configured to radiate at the same bandwidth or a different bandwidth. The plurality of antennas may be positioned on probe 201 in a symmetric manner or non-symmetric manner.

It is expected that during the life of a patent maturing from this application many relevant devices and methods will be developed and the scope of the term a catheter, a probe, an antenna, a transmission point, and a receiving point is intended to include all such new technologies a priori.

As used herein, if a machine (e.g., a processor) is described as "configured to" perform a task (e.g., configured to calculate a transmission pattern), then, at least in some embodiments, the machine may include components, parts, or aspects (e.g., software) that enable the machine to perform a particular task. In some embodiments, the machine may perform this task during operation. Similarly, when a task is described as being done "in order to" establish a target result, then, at least in some embodiments, carrying out the task may accomplish the target result.

As used herein the term "about" refers to ±10%.

The terms "comprises", "comprising", "includes", "including", "having" and their conjugates mean "including but not limited to". This term encompasses the terms "consisting of" and "consisting essentially of".

As used herein, the singular form "a", "an" and "the" include plural references unless the context clearly dictates otherwise. For example, the term "an antenna" or "at least one antenna" may include a plurality of antenna, including compound antenna.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Citation or identification of any reference in this application shall not be construed as an admission that such reference is available as prior art to the present invention. To the extent that section headings are used, they should not be construed as necessarily limiting.

What is claimed is:

1. A system of intrabody treatment, comprising:
    a multi point probe transported by a catheter to a lumen of a body of a treated patient, the multi point probe having at least two transmission points; and
    a processor configured to:
        select a transmission pattern including for each of the at least two transmission points, a respective signal of a plurality of radio frequency transmission signals, said transmission pattern forms at least one interaction between the respective signals from the at least two transmission points, the at least one interaction defines at least one hot spot at the treatment location; and
        control delivery of the respective signals from the transmission points;
    wherein the processor determines a timing for each of said respective signals.

2. A system of intrabody treatment, comprising:
    a multi point probe transported by a catheter to a lumen of a body of a treated patient, the multi point probe having at least two transmission points; and
    a processor configured to:
        select a transmission pattern including for each of the at least two transmission points, a respective signal of a plurality of radio frequency transmission signals, said transmission pattern forms at least one interaction between the respective signals from the at least two transmission points, the at least one interaction defines at least one hot spot at the treatment location; and
        control delivery of the respective signals from the transmission points, wherein the processor selects said respective signals to interact concurrently.

3. The system of claim 1, wherein the multi point probe has a supporting structure having a compressed state to allow placing the multi point probe in a lumen of the catheter and a deployed stated that place the at least two transmission points away from one another and from a longitudinal axis of the lumen.

4. The system of claim 3, wherein said multi point probe includes one or more receiving points supported by said supporting structure intercepting an energy from said treatment location.

5. The system of claim 4, wherein at least one of said one or more receiving points is also one of said at least two transmission points.

6. The system of claim 1, further comprising:
    an energy source controlled by said processor; said energy source supplying said respective signals to said transmission points.

7. A method of intrabody treating a treatment location in a body of a treated patient, comprising:

deploying at least two transmission points of a multi point probe to a proximity with the treatment location in the body;

selecting a transmission pattern that defines, for each of the at least two transmission points, a respective signal of a plurality of radio frequency transmission signals, the transmission pattern forms at least one interaction between said respective signals; wherein the at least one interaction is selected to form at least one hot spot at the treatment location; and delivering the respective signals from the at least two transmission points, wherein the selecting a transmission pattern comprises defining at least one of a phase, frequency and input power of each said respective signal.

8. The method of claim 7, wherein said delivering of at least two of said respective signals is concurrent.

9. The method of claim 7, wherein said selecting further includes selecting a timing for said delivering and said delivering of said respective signals is at different times.

10. The method of claim 9, wherein said different times are chosen to increase interaction for a target selected from the group consisting of a particular chemical, a particular tissue and a particular location.

11. The method of claim 7, wherein the delivering of each of at least two of said interacting respective signals is from a different respective points of said at least two transmission points.

12. The method according to claim 7, wherein the at least one interaction is selected from the group consisting of constructive interference, spatial interaction, temporal interaction, signal correlation, resonance and destructive interference that defines the at least one hot spot.

13. A method of intrabody treating a treatment location in a body of a treated patient, comprising:

deploying at least two transmission points of a multi point probe to a proximity with the treatment location in the body;

selecting a transmission pattern that defines, for each of the at least two transmission points, a respective signal of a plurality of radio frequency transmission signals, the transmission pattern forms at least one interaction between said respective signals; wherein the at least one interaction is selected to form at least one hot spot at the treatment location; and delivering the respective signals from the at least two transmission points, wherein the multi point probe includes a plurality of receiving points for intercepting energy delivered from the at least two transmission points via the treatment location and the method further comprising:

measuring said intercepted energy.

14. The method of claim 13, further including:

creating a map of a dielectric property in at least a part of said treatment location according to an analysis of said intercepted energy.

15. The method of claim 13, wherein the transmission pattern is selected according to a result of said measuring.

16. The method according to claim 13, further comprising:

measuring a complex impedance that includes real and imaginary parts at least one of said transmission points and wherein the selecting is performed according to both the real and imaginary parts.

17. The method of claim 14, wherein the selecting is performed according to a combination of the map of the dielectric property in the at least a part of said treatment location and an anatomical map mapping of at least part of the treatment location.

18. A method of intrabody treating a treatment location in a body of a treated patient, comprising:

deploying at least two transmission points of a multi point probe to a proximity with the treatment location in the body;

selecting a transmission pattern that defines, for each of the at least two transmission points, a respective signal of a plurality of radio frequency transmission signals, the transmission pattern forms at least one interaction between said respective signals; wherein the at least one interaction is selected to form at least one hot spot at the treatment location; and delivering the respective signals from the at least two transmission points, wherein the delivering comprises detecting changes in a dielectric property of the treatment location or of data received by a receiving point and an adjustment of said delivering according to the detecting.

19. The method of claim 7, wherein the delivering comprises transmitting three different said respective signals from three different transmission points.

20. The method of claim 7, wherein said delivering is simultaneous.

21. The method of claim 7, wherein at least one of the at least two transmission signals includes a microwave band signal.

22. The method of claim 7, further including:

directing said delivering with an artificial dielectric located inside said patient.

23. A method of intrabody imaging in a body of a treated patient, comprising:

inserting a probe into the body, the probe including at least two transmission points;

delivering a radio frequency transmission signal from the at least two transmission points into the treatment location;

intercepting by at least one receiving point a feedback from at least one of said respective signals via the treatment location; and reconstructing at least one dielectric property of a tissue in a treatment location and of at least one additional tissue in said treatment location based on the intercepted feedback.

24. The method of claim 23, wherein reconstructing comprises identifying fat areas.

25. The method of claim 23, wherein reconstructing comprises identifying a movement of the probe.

26. The method of claim 23, wherein the delivering comprises transmitting in sequence from at least three different transmission points of said probe.

27. The method of claim 23, further including:

directing said delivering with an artificial dielectrics located inside the patient.

28. The method of claim 23, wherein each said transmission point is separately connected to an EM energy source for separately receiving one of the plurality of transmission signals.

* * * * *